United States Patent
Molnar

(10) Patent No.: US 11,052,018 B2
(45) Date of Patent: Jul. 6, 2021

(54) TEMPERATURE ACTIVATED VIBRATING CAPSULE FOR GASTROINTESTINAL TREATMENT, AND A METHOD OF USE THEREOF

(71) Applicant: VIBRANT LTD., Yokneam (IL)

(72) Inventor: Shai Molnar, Shorashim (IL)

(73) Assignee: Vibrant Ltd., Yokneam (IL)

( * ) Notice: Subject to any disclaimer, the term of this patent is extended or adjusted under 35 U.S.C. 154(b) by 0 days.

(21) Appl. No.: 16/780,923

(22) Filed: Feb. 4, 2020

(65) Prior Publication Data

US 2020/0246216 A1 Aug. 6, 2020

(30) Foreign Application Priority Data

Feb. 4, 2019 (GB) .................................. 1901470

(51) Int. Cl.
*A61H 21/00* (2006.01)
*A61H 23/02* (2006.01)

(52) U.S. Cl.
CPC ......... *A61H 21/00* (2013.01); *A61H 23/0263* (2013.01); *A61H 2201/5005* (2013.01);
(Continued)

(58) Field of Classification Search
None
See application file for complete search history.

(56) References Cited

U.S. PATENT DOCUMENTS 3,485,235 A 12/1969 Felson
4,507,115 A 3/1985 Kambara et al.
(Continued)

FOREIGN PATENT DOCUMENTS

CN 1829466 A 9/2006
CN 102743174 A 10/2012
(Continued)

OTHER PUBLICATIONS

Smart capsule to target colon diseases, Ben Gruber, Sep. 30, 2015 ,Reuters Health News.
(Continued)

*Primary Examiner* — Bradley H Philips
*Assistant Examiner* — Savannah L Gabriel
(74) *Attorney, Agent, or Firm* — Marc Van Dyke; Momentum IP

(57) ABSTRACT

A vibrating ingestible capsule includes a housing having a longitudinal axis, and having a vibrating agitator adapted such that, in a first vibrating mode of operation, the housing exerts vibrations on an environment surrounding the capsule. A power supply disposed within the housing is adapted to power the vibrating agitator. A temperature sensor provides temperature information signals with respect to a temperature in an environment surrounding the vibrating ingestible capsule over a period of time. A control element is adapted to receive the temperature information signals from the temperature sensor, to identify a current temperature-over-time pattern based on the temperature information signals received from said temperature sensor, to compare the current temperature-over-time pattern to a predetermined temperature-over-time pattern, and, after the current temperature-over-time matches the predetermined temperature-over-time pattern, to activate the vibrating agitator to operate in the first vibrating mode of operation.

13 Claims, 2 Drawing Sheets

(52) U.S. Cl.
CPC .......... *A61H 2201/5025* (2013.01); *A61H 2201/5082* (2013.01); *A61H 2201/5084* (2013.01); *A61H 2201/5097* (2013.01)

(56) References Cited

U.S. PATENT DOCUMENTS

| | | | |
|---|---|---|---|
| 5,170,801 | A | 12/1992 | Casper et al. |
| 6,632,216 | B2 | 10/2003 | Houzego et al. |
| 6,776,165 | B2 | 8/2004 | Jin |
| 6,929,363 | B2 | 8/2005 | Sakai et al. |
| 6,984,205 | B2 | 1/2006 | Gazdzinski |
| 8,202,697 | B2 | 6/2012 | Holmes |
| 8,518,022 | B2 | 8/2013 | Trovato et al. |
| 8,597,278 | B2 | 12/2013 | Trovato et al. |
| 8,701,677 | B2 | 4/2014 | Duan et al. |
| 8,771,730 | B2 | 7/2014 | Navon |
| 9,078,799 | B2 | 7/2015 | Shohat et al. |
| 9,156,169 | B2 | 10/2015 | Duan et al. |
| 9,232,909 | B2 | 1/2016 | Duan et al. |
| 9,532,923 | B2 | 1/2017 | Shohat et al. |
| 9,707,150 | B2 | 7/2017 | Shabbat |
| 2002/0132226 | A1 | 9/2002 | Nair et al. |
| 2003/0020810 | A1 | 1/2003 | Takizawa et al. |
| 2004/0030454 | A1 | 2/2004 | Kim et al. |
| 2004/0253304 | A1 | 12/2004 | Gross et al. |
| 2004/0267240 | A1 | 12/2004 | Gross et al. |
| 2005/0058701 | A1 | 3/2005 | Gross et al. |
| 2005/0085696 | A1 | 4/2005 | Uchiyama et al. |
| 2005/0148847 | A1 | 7/2005 | Uchiyama et al. |
| 2005/0177069 | A1 | 8/2005 | Takizawa et al. |
| 2006/0169293 | A1 | 8/2006 | Yokoi et al. |
| 2006/0276729 | A1 | 12/2006 | Reed et al. |
| 2007/0015952 | A1 | 1/2007 | Chang et al. |
| 2007/0238940 | A1 | 10/2007 | Amirana |
| 2008/0188837 | A1 | 8/2008 | Belsky et al. |
| 2008/0275430 | A1 | 11/2008 | Belsky et al. |
| 2009/0281380 | A1 | 11/2009 | Miller et al. |
| 2009/0306633 | A1 | 12/2009 | Trovato et al. |
| 2009/0318841 | A1* | 12/2009 | Shohat ............ A61H 23/02 601/46 |
| 2010/0049012 | A1 | 2/2010 | Dijksman et al. |
| 2010/0217079 | A1 | 8/2010 | Tichy |
| 2010/0324381 | A1* | 12/2010 | Glukhovsky ........ A61B 1/04 600/302 |
| 2013/0267788 | A1 | 10/2013 | Duan et al. |
| 2015/0011829 | A1 | 1/2015 | Wang et al. |
| 2015/0011874 | A1* | 1/2015 | Amoako-Tuffour ............ A61B 5/065 600/424 |
| 2015/0018614 | A1 | 1/2015 | Duan et al. |
| 2015/0018615 | A1 | 1/2015 | Duan et al. |
| 2015/0073315 | A1 | 3/2015 | Shabbat |
| 2015/0380140 | A1 | 12/2015 | Duan et al. |
| 2016/0287058 | A1 | 10/2016 | Ye et al. |
| 2016/0310357 | A1 | 10/2016 | Duan et al. |
| 2017/0020374 | A1 | 1/2017 | Duan et al. |
| 2017/0035407 | A1 | 2/2017 | Duan et al. |
| 2017/0035520 | A1 | 2/2017 | Duan et al. |
| 2017/0135897 | A1 | 5/2017 | Shohat et al. |
| 2017/0273863 | A1 | 9/2017 | Shabbat |
| 2017/0296425 | A1 | 10/2017 | Duan et al. |
| 2017/0296428 | A1* | 10/2017 | Duan ............ A61H 23/0263 |
| 2017/0340242 | A1 | 11/2017 | Duan |
| 2018/0055597 | A1 | 3/2018 | Duan et al. |
| 2018/0084975 | A1 | 3/2018 | Duan et al. |
| 2018/0168490 | A1* | 6/2018 | Jones ............ A61B 5/7282 |
| 2018/0185238 | A1* | 7/2018 | Ilan ............ A61N 1/36007 |
| 2019/0224070 | A1 | 7/2019 | Ben-Tsur et al. |
| 2019/0307999 | A1 | 10/2019 | Ben-Tsur |
| 2019/0308002 | A1 | 10/2019 | Ben-Tsur |

FOREIGN PATENT DOCUMENTS

| | | |
|---|---|---|
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105411505 A | 3/2016 |
| CN | 205108749 U | 3/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2010503451 A | 2/2010 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2013121276 A1 | 8/2013 |
| WO | 2018055487 A1 | 3/2018 |

OTHER PUBLICATIONS

Advanced Delivery Devices—IntelliCap: An Intelligent, Electronic Capsule for Oral Drug Delivery & Development, Drug Development & Delivery, Apr. 2013.
Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct. 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.

(56) References Cited

OTHER PUBLICATIONS

Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 23, 2016.
Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017.
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6, 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.
Co-pending U.S. Appl. No. 15/882,283, filed Jan. 29, 2018.
Co-pending U.S. Appl. No. 15/882,289, filed Jan. 29, 2018.
Co-pending U.S. Appl. No. 15/882,329, filed Jan. 29, 2018.
Co-pending U.S. Appl. No. 16/403,553, filed May 5, 2019.
Co-pending U.S. Appl. No. 15/882,552, filed Jan. 29, 2018.
Co-pending U.S. Appl. No. 16/747,635, filed Jan. 21, 2020.
Co-pending U.S. Appl. No. US 16/732,883, filed Jan. 2, 2020.
Co-pending U.S. Appl. No. 16/823,035, filed Mar. 18, 2020.
Co-pending U.S. Appl. No. 16/377,213, filed Apr. 7, 2019.

* cited by examiner

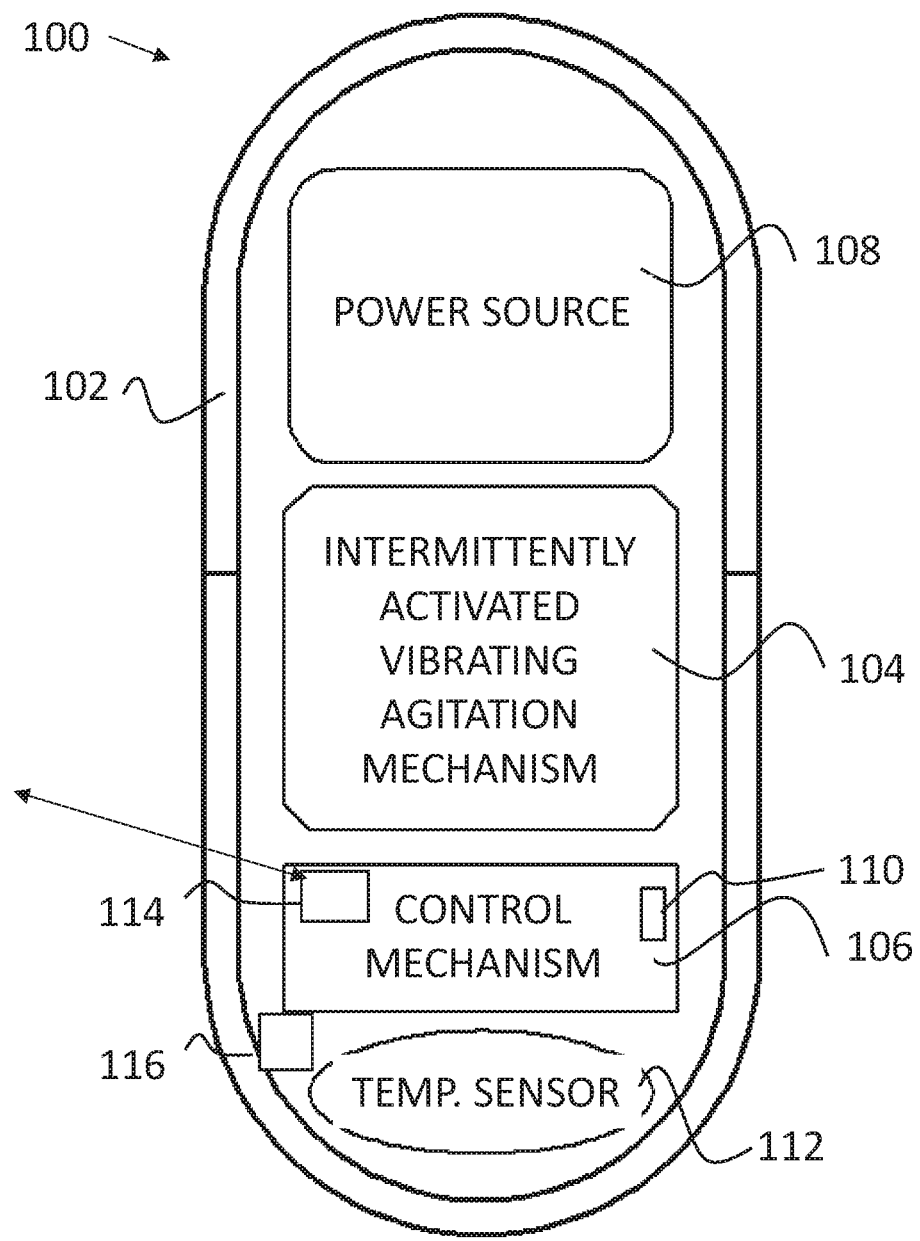

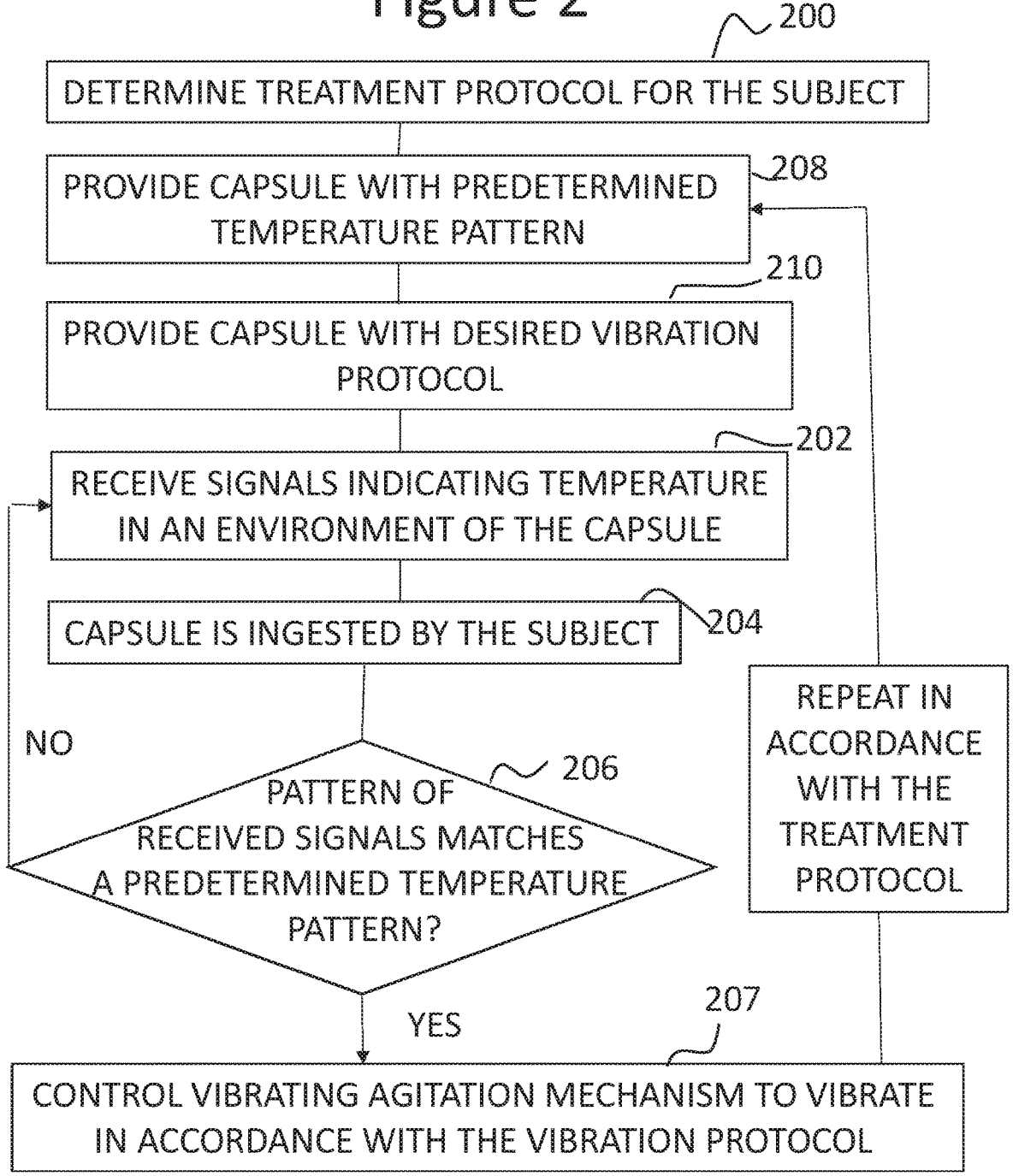

TEMPERATURE ACTIVATED VIBRATING CAPSULE FOR GASTROINTESTINAL TREATMENT, AND A METHOD OF USE THEREOF

RELATED APPLICATIONS

The present application gains priority from GB Patent Application Number 1901470.3 filed Feb. 4, 2019 and entitled A TEMPERATURE ACTIVATED VIBRATING CAPSULE FOR GASTROINTESTINAL TREATMENT, AND A METHOD OF USE THEREOF.

FIELD OF THE INVENTION

The present invention relates in general to vibrating capsules for gastrointestinal treatment and to methods of use thereof, and more particularly, to vibrating capsules for gastrointestinal treatment whose vibration is activated by tracking the temperature of the environment surrounding the capsule.

SUMMARY OF THE INVENTION

In accordance with an embodiment of the present invention, there is provided a vibrating ingestible capsule including:
(a) a housing having a longitudinal axis;
(b) a vibrating agitator adapted such that, in a first vibrating mode of operation, the housing exerts vibrations on an environment surrounding the capsule;
(c) a power supply disposed within the housing and adapted to power the vibrating agitator;
(d) a temperature sensor adapted to provide temperature information signals with respect to a temperature in an environment surrounding the vibrating ingestible capsule, over a period of time; and
(e) a control element adapted to:
   receive the temperature information signals from the temperature sensor;
   identify a current temperature-over-time pattern based on the temperature information signals received from the temperature sensor;
   compare the current temperature-over-time pattern to a predetermined temperature-over-time pattern; and
   after the current temperature-over-time pattern matches the predetermined temperature-over-time pattern, activate the vibrating agitator to operate in the first vibrating mode of operation.

In some embodiments, the control element is adapted to activate the vibrating agitator to operate in the first vibrating mode of operation immediately upon determining that the current temperature-over-time pattern matches the predetermined temperature-over-time pattern. In other embodiments, the control element is adapted to activate the vibrating agitator to operate in the first vibrating mode of operation a predetermined duration after determining that the current temperature-over-time pattern matches the predetermined temperature-over-time pattern.

In some embodiments, the predetermined temperature-over-time pattern includes a transition of the capsule from an environment having a temperature distinct from human body temperature to an environment having human body temperature, followed by a predetermined duration at which a temperature of the environment is stable at human body temperature.

In some embodiments, the predetermined duration is in the range of 15 minutes to 100 hours, 15 minutes to 1 hour, 15 minutes to 45 minutes, 15 minutes to 30 minutes, 2 hours to 48 hours, 2 hours to 42 hours, 2 hours to 36 hours, 2 hours to 30 hours, 2 hours to 24 hours, 3 hours to 24 hours, 4 hours to 24 hours, 4 hours to 20 hours, 4 hours to 18 hours, 4 hours to 16 hours, 4 hours to 14 hours, 4 hours to 12 hours, 6 hours to 12 hours, 6 hours to 10 hours, 40 hours to 100 hours, 50 hours to 100 hours, 60 hours to 100 hours, or 60 hours to 90 hours.

In some embodiments, the capsule includes at least one timing mechanism functionally associated with the control element or with the temperature sensor, and is adapted to identify times at which the temperature information signals are provided by the temperature sensor or are received by the control element.

In some embodiments, when the vibrating agitator is operative in the first vibrating mode of operation, vibration is in accordance with a vibration protocol.

In some embodiments, the vibration protocol includes a default vibration protocol, pre-programmed into at least one of the vibrating agitator and the control element.

In some embodiments, the vibration protocol is provided to the control element from a remote location, prior to activation of the vibrating agitator to operate in the first vibrating mode of operation.

In some embodiments, the temperature sensor is adapted to begin providing the temperature information signals only in response to a triggering event. In some embodiments, the vibrating ingestible capsule further includes at least one other sensor operative to provide a triggering signal indicative of occurrence of the triggering event.

In some embodiments, the at least one other sensor includes at least one of a motion sensor and a three dimensional orientation sensor, adapted to provide a triggering signal indicative of a triggering motion carried out by a user on the capsule as the triggering event. In some embodiments, the at least one other sensor includes an illumination sensor, adapted to provide a triggering signal indicating the capsule moving from a dark environment to an illuminated environment as the triggering event.

In some embodiments, the temperature sensor is adapted to provide the temperature information signals periodically. In some embodiments, the temperature sensor is adapted to provide the temperature information signals at a frequency of once every hour, once every 30 minutes, once every 20 minutes, once every 15 minutes, once every 10 minutes, once every 5 minutes, or once every minute.

In some embodiments, the power supply is adapted to power the temperature sensor, and wherein a power of the power supply is sufficient to power the temperature sensor to provide the temperature information signals at the frequency for a duration of at least one month, at least three months, at least six months, or at least a year, while maintaining sufficient charge for operation of the vibrating agitator in the first vibrating mode of operation for at least a predetermined cumulative vibrating duration. In some embodiments, the predetermined cumulative vibrating duration is in the range of 1 hour to 12 hours, 2 hours to 10 hours, 2 hours to 8 hours, 2 hours to 6 hours, 2 hours to 4 hours, or 2 hours to 3 hours.

In some embodiments, the vibrating ingestible capsule further includes a sensor power supply, different from the power supply, adapted to power the temperature sensor to provide the temperature information signals at the frequency for a duration of at least one month, at least three months, at least six months, or at least a year.

In some embodiments, the vibrating agitator includes at least a radial agitation mechanism adapted, in the first vibrating mode of operation, to exert radial forces on the housing, in a radial direction with respect to the longitudinal axis of the housing, thereby to cause the vibrations exerted by the housing.

In some embodiments, the vibrating agitator includes at least an axial agitation mechanism adapted, in the first vibrating mode of operation, to exert axial forces on the housing, in an axial direction with respect to the longitudinal axis of the housing, thereby to cause the vibrations exerted by the housing.

In some embodiments, the vibrating agitator is adapted in the first vibrating mode of operation, to exert radial forces on the housing in a radial direction with respect to the longitudinal axis of the housing and to exert axial forces on the housing in an axial direction with respect to the longitudinal axis of the housing, thereby to cause the vibrations exerted by the housing.

In some embodiments, the vibrating agitator includes a radial agitation mechanism adapted to exert the radial forces and a separate axial agitation mechanism adapted to exert the axial forces.

In some embodiments, the vibrating agitator includes a single agitation mechanism adapted to exert the radial forces and the axial forces.

In some embodiments, the vibrating mode of operation including a plurality of cycles, each of the cycles including a vibration duration followed by a repose duration, wherein the housing exerts the vibrations during the vibration duration. In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, the vibrating agitator is configured such that a net force exerted by the housing on the environment is in the range of 50 grams-force to 600 grams-force.

In some embodiments, the vibrating agitator is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the controlling of the vibrating agitator is effected so as to effect a mechanical stimulation of the wall of the gastrointestinal tract.

In accordance with another embodiment of the present invention, there is provided a method of treating an ailment of the gastrointestinal tract of a subject, the method including:
(a) providing the vibrating ingestible capsule as described herein;
(b) ingesting the vibrating ingestible capsule; and
(c) controlling the vibrating agitator such that activation of the vibrating agitator to operate in the first vibrating mode of operation occurs after a current temperature-over-time pattern formed based on temperature information signals received from the temperature sensor matches a predetermined temperature-over-time pattern.

In accordance with yet another embodiment of the present invention, there is provided a method of treating an ailment of the gastrointestinal tract of a subject, the method including:
(a) providing a vibrating ingestible capsule, adapted to transit a gastrointestinal tract of the subject, the capsule having:
   (1) a housing having a longitudinal axis;
   (2) a vibrating agitator adapted such that, in a first vibrating mode of operation, the housing exerts vibrations on an environment surrounding the capsule;
   (3) a power supply disposed within the housing and adapted to power the vibrating agitator;
   (4) a temperature sensor adapted to provide temperature information signals with respect to a temperature in an environment surrounding the vibrating ingestible capsule, over a period of time; and
   (5) a control element adapted to receive the temperature information signals from the temperature sensor, to identify a current temperature-over-time pattern based on the temperature information signals received from the temperature sensor, to compare the current temperature-over-time pattern to a predetermined temperature-over-time pattern, and to activate the vibrating agitator to operate in the first vibrating mode of operation;
(b) providing temperature information signals with respect to a temperature in an environment surrounding the vibrating ingestible capsule from the temperature sensor to the control element;
(c) ingesting the gastrointestinal capsule; and
(d) after a current temperature-over-time pattern based on the temperature information signals received from the temperature sensor matches the predetermined temperature-over-time pattern, controlling the vibrating agitator to operate in the first vibrating mode of operation.

In some embodiments, controlling the vibrating agitator to operate in the first vibrating mode of operation occurs immediately upon the control element determining that the current temperature-over-time pattern matches the predetermined temperature-over-time pattern. In other embodiments, controlling the vibrating agitator to operate in the first vibrating mode of operation occurs a predetermined duration after the control element determining that the current temperature-over-time pattern matches the predetermined temperature-over-time pattern.

In some embodiments, the predetermined temperature-over-time pattern includes a transition of the capsule from an environment having a temperature distinct from human body temperature to an environment having human body temperature, followed by a predetermined duration at which a temperature of the environment is stable at human body temperature. In some embodiments, the predetermined duration is in the range of 15 minutes to 100 hours, 15 minutes to 1 hour, 15 minutes to 45 minutes, 15 minutes to 30 minutes, 2 hours to 48 hours, 2 hours to 42 hours, 2 hours to 36 hours, 2 hours to 30 hours, 2 hours to 24 hours, 3 hours to 24 hours, 4 hours to 24 hours, 4 hours to 20 hours, 4 hours to 18 hours, 4 hours to 16 hours, 4 hours to 14 hours, 4 hours to 12 hours, 6 hours to 12 hours, 6 hours to 10 hours, 40 hours to 100 hours, 50 hours to 100 hours, 60 hours to 100 hours, or 60 hours to 90 hours.

In some embodiments, the controlling includes controlling the vibrating agitator to vibrate in accordance with a vibration protocol when operative in the first vibrating mode of operation. In some embodiments, the method further includes providing the vibration protocol to the control element from a remote location, prior to the controlling.

In some embodiments, providing the temperature information signals is initiated only in response to a triggering event. In some embodiments, the vibrating ingestible capsule further includes at least one other sensor, and the method further includes, prior to the providing, receiving, from the at least one other sensor, a triggering signal indicating occurrence of the triggering event.

In some embodiments, receiving the triggering signal includes receiving a triggering signal indicating a triggering motion carried out by a user on the capsule.

In some embodiments, receiving the triggering signal includes receiving a triggering signal indicating the capsule moving from a dark environment to an illuminated environment.

In some embodiments, providing the temperature information signals includes providing the temperature information signals periodically. In some embodiments, providing the temperature information signals includes providing the temperature information signals at a frequency of once every hour, once every 30 minutes, once every 20 minutes, once every 15 minutes, once every 10 minutes, once every 5 minutes, or once every minute.

In some embodiments, the vibrating agitator includes at least a radial agitation mechanism, and the controlling includes controlling the radial agitation mechanism, in the first vibrating mode of operation, to exert radial forces on the housing, in a radial direction with respect to the longitudinal axis of the housing, thereby to cause the vibrations exerted by the housing.

In some embodiments, the vibrating agitator includes at least an axial agitation mechanism, and the controlling includes controlling the axial agitation mechanism, in the first vibrating mode of operation, to exert axial forces on the housing, in an axial direction with respect to the longitudinal axis of the housing, thereby to cause the vibrations exerted by the housing.

In some embodiments, controlling includes controlling the vibrating agitator, in the first vibrating mode of operation, to exert radial forces on the housing in a radial direction with respect to the longitudinal axis of the housing and to exert axial forces on the housing in an axial direction with respect to the longitudinal axis of the housing, thereby to cause the vibrations exerted by the housing.

In some embodiments, controlling the vibrating agitator includes controlling the vibrating mode of operation to include a plurality of cycles, each of the cycles including a vibration duration followed by a repose duration, wherein the housing exerts the vibrations during the vibration duration. In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, controlling the vibrating agitator includes controlling the vibrating agitator such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, in the first vibration mode of operation, the vibrating agitator is configured such that a net force exerted by the housing on the environment is in the range of 50 grams-force to 600 grams-force.

In some embodiments, in the first vibration mode of operation the vibrating agitator is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, controlling of the vibrating agitator includes controlling the vibrating agitator so as to effect a mechanical stimulation of the wall of the gastrointestinal tract.

In some embodiments, the method further includes, prior to the ingesting of the vibrating ingestible capsule, providing the predetermined temperature-over-time pattern to the control element of the vibrating ingestible capsule.

BRIEF DESCRIPTION OF THE FIGURES

The foregoing discussion will be understood more readily from the following detailed description of the invention, when taken in conjunction with the accompanying FIGS. 1-2), in which:

FIG. 1 is a schematic block diagram of a vibrating ingestible capsule according to an embodiment of the present invention; and FIG. 2 is a schematic flowchart of a method for treating an ailment of the gastrointestinal tract according to the present invention, the treatment being based on use of a vibrating ingestible capsule, for example as shown in FIG. 1.

DESCRIPTION OF THE PREFERRED EMBODIMENTS

The principles of the inventive vibrating ingestible capsule and method of treating ailments of the gastrointestinal tract using the inventive vibrating ingestible capsule, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this application, the term "subject" relates to a human. For the purposes of this application, the term "vibrating ingestible capsule" relates to an ingestible capsule adapted to vibrate, at least intermittently, for a cumulative duration of at least one minute, in accordance with a vibration protocol of the capsule.

For the purposes of this application, the term "vibrating agitator" refers to any type of mechanism that vibrates or causes elements in its vicinity to vibrate, including a motor driven agitator such as a motor driven eccentric weight or a motor driven pendulum.

For the purposes of this application, the term "intermittently activated vibrating agitator" refers to a vibration engine that vibrates and is operative at certain times, and does not vibrate at other times, the activation times being selected by a control element or other control unit controlling the vibration engine.

For the purposes of this application, the term "control element", and the equivalent term "controller" refer to a component for controlling operation of mechanical and/or electrical components of the capsule, which includes a processing unit functionally associated with a non-tangible computer readable storage medium. The storage medium stores instructions, which, when executed by the processing unit, cause the processing unit to carry out actions which control the operation of the mechanical and/or electrical components of the capsule. For example, the instructions may include instructions to activate operation of a vibrating agitator at a specific time, frequency, cycle, and/or for a specific duration. The control element may be functionally associated with, or may include, a transceiver for receiving input, which input may be used to trigger execution of specific instructions stored in the storage medium.

For the purposes of this application, the term "vibration protocol" relates to a protocol specifying vibration parameters of an intermittently activated vibrating agitator of a vibrating ingestible capsule. Typically, the vibration protocol relates to an activation delay for initiating vibration (a duration between activation of the capsule and the first activation of the vibration engine), a vibration rate (number of vibration cycles per hour), a vibration duration and a repose duration for each vibration cycle, a vibration frequency, an amount of force exerted by the vibrations, and the like.

For the purposes of this application, the term "treatment procedure" relates to parameters of a treatment utilizing vibrating ingestible capsules, which are typically defined by a treating physician or medical practitioner. For example, the treatment procedure may include the number of capsules to be taken within a specific time duration (e.g. 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a subject with a vibrating ingestible capsule, and includes the treatment procedure as well as the vibration protocol to be used for treating the subject. For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a control element controlling vibration of the capsule is inactive.

For the purpose of this application, a vibrating ingestible capsule is said to be in an "operative state" when the control element of the capsule is processing inputs and data and can cause a vibrating agitator of the capsule to vibrate.

For the purpose of this application, the term "human body temperature" relates to a temperature in the range of 36.0° C. to 38.0° C.

For the purposes of this application, a temperature is considered to be "distinct" from given temperature if the temperature has a difference of more than 3.0° C., and typically greater than 2.0° C., 1.5° C., 1.2° C., or 1.0° C. from the given temperature. In other words, the temperature is distinct from the given temperature if it is more than 3.0° C., and typically greater than 2.0° C., 1.5° C., 1.2° C., or 1.0° C. above the given temperature or more than 3.0° C., and typically greater than 2.0° C., 1.5° C., 1.2° C., or 1.0° C. below the given temperature.

For the purposes of this application, a temperature is considered to be "stable" at a given temperature for a specific duration if, during the specific duration, the measured temperature does not have a difference greater than 3.0° C., and typically greater than 2.0° C., 1.5° C., 1.2° C., or 1.0° C. from the given temperature. In other words, within the specific duration the measured temperature is never more than 3.0° C., and typically greater than 2.0° C., 1.5° C., 1.2° C., or 1.0° C. above the given temperature or more than 3.0° C., and typically greater than 2.0° C., 1.5° C., 1.2° C., or 1.0° C. below the given temperature.

For the purposes of this application, two temperature-over-time patterns are considered to match one another if, for at least 90%, and typically for at least 92%, at least 95%, or at least 98%, of the points in time of the temperature-over-time pattern, the temperature difference between the temperatures in the two temperature-over-time patterns is not greater than 3.0° C., and typically not greater than 2.0° C., 1.5° C., 1.2° C., or 1.0° C.

For the purposes of this application, the term "dark environment" relates to an environment having substantially absolute darkness, or an illuminance of 0-0.5 LUX, as that found within a foil packaging of a medicament.

For the purposes of this application, the term "illuminated environment" relates to an environment having any level of illumination more than absolute darkness, the illumination provided by natural illumination sources such as daylight or moonlight or by artificial illumination sources such as electric lamps, light emitting diodes, and the like. In the context of the present application, an illuminated environment has an illuminance of at least 100 LUX.

For the purposes of the present application, the term an event A happens "immediately upon" an event B, if event A occurs within 5 seconds, and typically within 3 seconds, within 2 seconds, or within one second from occurrence of event B.

Referring now to the drawings, FIG. 1 is a schematic block diagram of a vibrating ingestible capsule 100 according to an embodiment of the present invention.

As seen in FIG. 1, vibrating ingestible capsule 100 includes a capsule housing or shell 102, arranged along a longitudinal axis 103 and having disposed therein a vibrating agitator 104. A control element 106 is adapted to control operation of the vibrating agitator 104, and at least one power source 108 provides power to vibrating agitator 104 and control element 106.

Power source 108 may be any suitable power source, such as one or more alkaline or silver oxide batteries, primary batteries, rechargeable batteries, capacitors and/or supercapacitors.

Intermittently activated vibrating agitator 104 is adapted to have a vibration mode of operation (also termed the first mode of operation) and a rest mode of operation (also termed the second mode of operation). In the vibration mode of operation, intermittently activated vibrating agitator 104 is adapted to exert forces on capsule housing 102, such that capsule housing 102 exerts vibrations on an environment surrounding capsule 100.

Vibrating ingestible capsule 100 further includes a temperature sensor 112, functionally associated with control element 106. Temperature sensor 112 is adapted to sense a temperature in an environment of capsule 100, and to provide temperature information signals with respect to the sensed temperature to control element 106.

It is a particular feature of the present invention that control element 106 is adapted to receive temperature information signals from temperature sensor 112, to identify a current temperature-over-time pattern based on the received temperature information signals, and to compare the current temperature-over-time pattern to a predetermined temperature-over-time pattern. The control element is further adapted, after identifying that the current temperature-over-time pattern matches a predetermined temperature-over-time pattern, to activate vibrating agitator 104 to operate in the vibrating mode of operation, as described in detail hereinbelow with respect to FIG. 2.

Typically, the capsule is in an inoperative state until activated by control element 106 following identification of a temperature-over-time pattern matching the predetermined temperature-over-time pattern.

In some embodiments, the predetermined temperature-over-time pattern includes a transition of the capsule from an environment having a temperature distinct from human body temperature to an environment having human body temperature, followed by a predetermined duration at which a temperature of the environment is stable at human body temperature.

In some embodiments, the predetermined duration is in the range of 15 minutes to 100 hours, 15 minutes to 1 hour, 15 minutes to 45 minutes, 15 minutes to 30 minutes, 2 hours to 48 hours, 2 hours to 42 hours, 2 hours to 36 hours, 2 hours to 30 hours, 2 hours to 24 hours, 3 hours to 24 hours, 4 hours to 24 hours, 4 hours to 20 hours, 4 hours to 18 hours, 4 hours to 16 hours, 4 hours to 14 hours, 4 hours to 12 hours, 6 hours to 12 hours, 6 hours to 10 hours, 40 hours to 100 hours, 50 hours to 100 hours, 60 hours to 100 hours, or 60 hours to 90 hours.

For example, consider a vibrating ingestible capsule 100 stored in a doctor's office or in a pharmacy until it is given to a subject for ingestion. Subsequently, the user drives home with the capsule, and ingests the capsule a few hours after arriving at home. The temperature sensor 112 would sense a temperature of approximately 25° C. (room temperature) while the capsule is in the pharmacy or doctor's office, and would then sense a different temperature when the user takes it out of the doctor's office and into the car. For example, during winter in Connecticut, while the user is outside, or just gets into his car, the temperature will likely be lower than 10° C., or even lower than 0° C. As another example, during the daytime in summer in Las Vegas, Nev., while the user is outside, or just gets into his car, the temperature will likely be higher than 40° C. When the user brings the capsule into his house, the temperature sensor would again sense a temperature of approximately 25° C. (room temperature), until the capsule is ingested by the user. Following ingestion by the user, temperature sensor would sense a temperature in the range of 36.0° C. to 38.0° C., which is human body temperature, until the capsule is expelled from the subject's body with feces. As such, while the capsule is within the body of the user, the temperature sensed by temperature sensor 112 will remain stable within the human body temperature range.

Since the temperature-over-time pattern described in the example matches the predetermined temperature-over-time pattern (first sense a temperature distinct from human body temperature, then sense a temperature equal to human body temperature for at least 6 hours), control element 106 identifies that the capsule has been ingested and is within the gastrointestinal tract for a predetermined duration, and activates the vibrating agitator to operate in the vibrating mode of operation at a suitable time following ingestion. In some embodiments, the suitable time may be immediately upon identification that the current temperature-over-time pattern matches the predetermined temperature-over-time pattern. In other embodiments, the suitable time may be a predetermined duration following identification that the current temperature-over-time pattern matches the predetermined temperature-over-time pattern.

As another example, consider a vibrating ingestible capsule 100 stored in a manufacturing facility, and then transported in a suitable vehicle to a doctor's office or to a pharmacy until it is given to a subject for ingestion, during summer months. The temperature sensor 112 would sense a temperature of approximately 25° C. (room temperature) while the capsule is in the manufacturing facility, and would then sense a different temperature when the capsule is being transported. In some cases, as discussed above, the different temperature may be higher than human body temperature (as in Las-Vegas during the summer) or lower than human body temperature (as in Connecticut during the winter). However, in some cases, the temperature during transportation may be similar to human body temperature, such as a temperature of 36-38° C., which may occur for example during the months of June and July in Tucson, Ariz. or in Dallas Tex. In such cases, the control element 106 may identify "human body temperature" during transportation of the capsule 100. However, because the temperature-over-time pattern requires stability at human body temperature for an extended duration, which typically does not occur during transportation, the temperature-over-time pattern is unlikely to be met during transportation. Once the capsule arrives at the pharmacy or doctor's office, the temperature sensed by sensor 112 would return to be approximately 25° C. (room temperature), causing the control element 106 to identify that the duration in which human body temperature was sensed is not indicative of ingestion of the capsule, and restarting to track for a time that the temperature-over-time pattern is met.

In some embodiments, at least one of control element 106 and temperature sensor 112 is functionally associated with, or includes, a timer or a timing mechanism 110, such as a clock, a universal clock, or a stopwatch, powered by power source 108. Timing mechanism 110 is adapted to track at least one time characteristic, such as a duration that has passed between receipt of one temperature information signal to receipt of another temperature information signal, a duration that the temperature information signals indicate a stable temperature, or to provide a timestamp to a received temperature information signal.

In some embodiments, control element 106 is adapted to control vibrating agitator 104 to operate in said first vibrating mode of operation in accordance with a vibration protocol.

In some such embodiments, the vibration protocol is a default vibration protocol, pre-programmed into vibrating agitator 104 and/or into control element 106. For example, the vibration protocol may be programmed into control element 106 by a manufacturer of capsule 100.

In other embodiments, control element 106 may be functionally associated with a remote input receiving mechanism 114, for example a transceiver, adapted to receive information relating to a desired vibration protocol from a remote location, prior to activation of vibrating agitator 104 to operate in said first vibrating mode of operation. For example, the vibration protocol may be transmitted to control element 106 via the transceiver from a computing device in a doctor's office, or from a remote control unit of the capsule 100 (not explicitly shown).

In some embodiments, the control unit may further include a timing mechanism adapted to track at least one time characteristic, such as a duration that has passed since a control instruction was provided to capsule 100.

In some embodiments, the control unit may further include a user input receiver, such as a keyboard, touch screen, or touch pad, adapted to receive input from a user, such as the user, a medical professional treating the user, or a caregiver of the user.

The control unit may be any suitable type of control unit. In some embodiments, control unit may be a suitably configured smart phone or a tablet computer.

In some such embodiments, the control unit may provide inputs to capsule 100 by remotely transmitting the inputs from an input providing mechanism to the remote input receiving mechanism 114, for example using a short range wireless communication method, such as radio frequency (RF) communication or Bluetooth® communication. One example of such a mechanism for providing input to a capsule is described in U.S. Pat. No. 10,478,373, which is incorporated by reference for all purposes as if fully set forth herein.

In some embodiments, the information relating to the vibration protocol may be remotely transmitted using a short-range wireless communication method. In some embodiments, the information relating to the vibration protocol is transmitted as a list of vibration parameters for effecting the vibration protocol. In some embodiments, the information relating to the vibration protocol is transmitted as executable code for effecting the vibration protocol.

In some embodiments, the information relating to the vibration protocol may include one or more of a desired number of vibration cycles, a desired vibration duration in each vibration cycle, a desired repose duration in each vibration cycle, a desired cumulative vibration duration, and the like.

In some embodiments, the predetermined temperature-over-time pattern to be used by control element 106 may be pre-programmed into the control element or may be remotely transmitted to the control element, for example from a remote control unit, substantially as described hereinabove with respect to the vibration protocol.

In some embodiments, temperature sensor 112 is adapted to begin sensing a temperature of the environment, and providing temperature information signals to control element 106, only in response to a triggering event. In some such embodiments, vibrating ingestible capsule 100 further includes at least one other sensor 116, functionally associated with control element 106 and/or with temperature sensor 112. The at least one other sensor 116 is adapted to provide to control element 106 an input, such as a triggering signal, indicating occurrence of the triggering event.

For example, in some embodiments, sensor 116 may include an illumination sensor, adapted to identify transition of capsule 100 from a dark environment (e.g. within a package) to an illuminated environment (e.g. outside the package) and to provide an input indicative of such a transition.

As another example, in some embodiments, sensor 116 may include a motion or acceleration sensor, such as an accelerometer, adapted to identify a triggering motion carried out by a user on capsule 100 and to provide an input indicative of such a motion.

In some embodiments, temperature sensor 112 is adapted to provide the temperature information signals to control element 106 periodically. For example, temperature sensor may provide the temperature information signals to control element 106 at a frequency of once every 3 hours, once every 2 hours, once every 1 hour, once every 30 minutes, once every 20 minutes, once every 15 minutes, once every 10 minutes, once every 5 minutes, or once every minute.

In some embodiments, power source 108 is also adapted to power temperature sensor 112. In such embodiments, the capacity of the power source 108 is sufficient to power temperature sensor 112 to provide the temperature information signals for a duration of at least one year, at least a year and a half, at least two years or at least two and a half years while maintaining sufficient capacity for operation of vibrating agitator 104 in the first vibrating mode of operation for at least a predetermined cumulative vibrating duration. In other words, power source must have enough power to enable temperature sampling by sensor 112 prior to activation the vibrating mode of operation of capsule 100, as well as to enable normal operation of the vibrating agitator.

In some such embodiments, the predetermined cumulative vibrating duration is in the range of 1 hour to 20 hours, 2 hours to 15 hours, 2 hours to 8 hours, 2 hours to 6 hours, 2 hours to 4 hours, or 2 hours to 3 hours.

In other embodiments, temperature sensor 112 is powered by a dedicated power source 118, which powers the temperature sensor to provide the temperature information signals. In some such embodiments, dedicated power source 118 has sufficient capacity to enable temperature sensor 112 to provide temperature information signals at the desired frequency for a duration of at least twelve months, at least eighteen months, at least twenty-four months, or at least a year.

Relating to the characteristics of vibrating agitator 104, the vibrating agitator may be any suitable mechanism that can be intermittently activated and can apply suitable forces onto capsule housing 102.

In some embodiments, intermittently activated vibrating agitator 104 may include a radial agitation mechanism adapted to exert radial forces on capsule housing 102, in a radial direction with respect to the longitudinal axis of housing 102. For example, the radial agitation mechanism may include an unbalanced weight attached to a shaft of an electric motor powered by a battery, substantially as described in U.S. Pat. No. 9,707,150, which is incorporated by reference for all purposes as if fully set forth herein.

In some embodiments, intermittently activated vibrating agitator 104 may include an axial agitation mechanism adapted to exert radial forces on the capsule housing 102, in an axial direction with respect to a longitudinal axis of housing 102. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitator 104 on capsule housing 102 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitator 104.

In some embodiments, the intermittently activated vibrating agitator 104 may include a magnet mounted onto a rotor adapted to exert a magnetic field as well as radial forces on capsule housing 102. For example, such a magnetic vibrating agitator is described in US Patent Application Publication No. 2016/0310357, which is incorporated by reference for all purposes as if fully set forth herein.

In some embodiments, housing 102 may include first and second members, and vibrating agitator 104 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In some embodiments, housing 102 may include a vibrating agitator 104 which makes use of a pendulum to cause vibration in the vicinity of the capsule, for example as described in CN Patent Application Number 105997466 filed on Jun. 16, 2016, which is incorporated by reference for all purposes as if fully set forth herein.

In the vibrating mode of operation, intermittently activated vibrating agitator 104 is adapted to have a plurality of vibration cycles, where each cycle includes a vibration duration followed by a repose duration. Forces are exerted by the vibrating agitator 104 on capsule housing 102 only during the vibration duration, and as such capsule housing 102 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration. In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, or 4 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 108.

It will be appreciated by persons skilled in the art that the vibration mode of operation may be intermittent, or interrupted, such that vibrating agitator 104 is operative in the vibration mode for a first duration, for example 30 minutes, then does have any vibration cycles for a second duration, for example 1 hour, and then is operative in the vibration mode and has vibration cycles for a third duration, for example two hours. The cumulative duration relates to the sum of all durations during which vibrating agitator 104 was operative in the vibration mode and included vibration cycles, including the vibration duration and the repose duration of the vibration cycle.

In some embodiments, vibrating agitator 104 is configured to exert forces on the capsule housing 102, such that a net force exerted by the capsule housing 102 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitator 104 is configured to exert said forces on capsule housing 102 to attain a capsule housing 102 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source and of the vibrating agitator.

It will be further appreciated that a specific capsule may be controlled by the control element such that different vibrational frequencies may be attained and/or different net forces may be exerted, by the capsule in different vibration cycles of the capsule. Due to the natural distinction between subjects, use of multiple different parameters in different vibration cycles of a single capsule would allow the capsule to successfully treat multiple subjects, even if the personal optimal treatment for those subjects is not the same, as there is a higher chance that in at least some of the vibration cycles the activation parameters of the capsule would reach, or be close to, the optimal parameters for each specific subject.

Control element 106 is adapted to control the operation of intermittently activated vibrating agitator 104. Such control may include control of any one or more of the force applied by the vibrating agitator, the vibrational frequency reached, the times in which vibrating agitator 104 operates in the vibration mode of operation, the vibration duration of each vibration cycle, the repose duration of each vibration cycle, the vibration cycle duration, and cumulative vibration duration of the vibrating agitators.

In some embodiments, control element 106 is adapted to control vibrating agitator 104 so that the capsule applies forces to an environment thereof to effect a mechanical stimulation of the wall of the gastrointestinal tract of the subject at the predetermined time(s).

Reference is now additionally made to FIG. 2, which is a schematic flowchart of a method for treating an ailment of the gastrointestinal tract according to the present invention, the treatment being based on use of a vibrating ingestible capsule, such as vibrating ingestible capsule 100 of FIG. 1.

It will be appreciated by people of skill in the art that the method described herein may be used for treatment of various ailments of the gastrointestinal tract, including constipation, a sensation of straining while defecating, a sensation of gastric bloating, and gastroparesis.

Initially, at step 200, the treatment protocol for the subject may be determined and/or obtained, for example by a treating physician or medical practitioner. The treatment protocol may indicate the number of treatment sessions per week or per other time duration, the time of day at which a capsule should be ingested, and/or may indicate the vibration protocol of the capsule.

At step 202, temperature information signals with respect to a temperature in an environment surrounding the capsule are received by the control element of the capsule (e.g. control element 106 of FIG. 1) from the temperature sensor of the capsule (e.g. sensor 112 of FIG. 1), over a period of time.

The capsule is provided to the subject and is ingested thereby at step 204.

At step 206, the control element determines whether or not a current temperature-over-time pattern based on the temperature information signals received from the temperature sensor matches a predetermined temperature-over-time pattern.

After determining that the current temperature-over-time pattern matches the predetermined temperature-over-time pattern, the control element controls the vibrating agitator of the capsule (e.g. vibrating agitator 104 of FIG. 1) to operate in the vibrating mode of operation at step 207. Otherwise, the control element awaits receipt of additional temperature information signals from the temperature sensor.

In some embodiments, providing temperature information signals from the temperature sensor at step 202 occurs before and/or during providing the capsule to the subject at step 200, ingesting the capsule by the subject at step 204, and/or determination by the control element at step 206.

In some embodiments, at step 202 the temperature sensor provides the temperature information signals periodically, i.e. at a fixed period. In some embodiments, the fixed period is once every 3 hours, once every 2 hours, once every one hour, once every 30 minutes, once every 20 minutes, once every 15 minutes, once every 10 minutes, once every 5 minutes, or once every minute.

In some embodiments, the predetermined temperature-over-time pattern identified by the control element at step 206 includes a transition of the capsule from an environment having a temperature distinct from human body temperature 36.0° C.-38.0° C. to an environment having human body temperature, followed by a predetermined duration at which a temperature of the environment is stable at human body temperature.

In some such embodiments, the predetermined duration at which the temperature of the environment is stable at human body temperature is in the range of 15 minutes to 100 hours, 15 minutes to 1 hour, 15 minutes to 45 minutes, 15 minutes to 30 minutes, 2 hours to 48 hours, 2 hours to 42 hours, 2 hours to 36 hours, 2 hours to 30 hours, 2 hours to 24 hours, 3 hours to 24 hours, 4 hours to 24 hours, 4 hours to 20 hours, 4 hours to 18 hours, 4 hours to 16 hours, 4 hours to 14 hours, 4 hours to 12 hours, 6 hours to 12 hours, 6 hours to 10 hours, 40 hours to 100 hours, 50 hours to 100 hours, 60 hours to 100 hours, or 60 hours to 90 hours.

In some embodiments, prior to the control element identifying the predetermined temperature-over-time pattern at step 206, the predetermined temperature-over-time pattern is provided to the capsule at step 208.

In some embodiments, the predetermined temperature-over-time pattern is provided to the capsule by pre-programming the predetermined temperature-over-time pattern into the control element, for example during manufacturing of the control element or of the capsule, in which case step 208 occurs prior to all of steps 200, 202, 204, and 207.

In some embodiments, the predetermined temperature-over-time pattern is provided to the capsule by transmitting the predetermined temperature-over-time pattern to the capsule from a remote location, such as a medical practitioner's computer or a remote control unit of the capsule. In such embodiments, step 208 may occur at any time prior to use of the predetermined temperature-over-time pattern, also after the capsule has been provided to the subject at step 200 and possibly even after the capsule has been ingested by the subject at step 204.

In some embodiments, controlling of the vibrating agitator at step 206 includes controlling the vibrating agitator, when operative in the vibrating mode of operation, to vibrate in accordance with a vibration protocol.

In some embodiments, prior to the control element controlling the vibrating agitator at step 207, the vibration protocol is provided to the capsule at step 210.

In some embodiments, the vibration protocol is provided to the capsule by pre-programming the protocol into the control element, for example during manufacturing of the control element or of the capsule, in which case step 210 occurs prior to all of steps 202, 204, and 207.

In some embodiments, the vibration protocol is provided to the capsule by transmitting the protocol to the capsule from a remote location, such as a medical practitioner's computer or a remote control unit of the capsule. In such embodiments, step 210 may occur at any time prior to use of the vibration protocol at step 207, also after the capsule has been provided to the subject at step 200 and possibly even after the capsule has been ingested by the subject at step 204.

In some embodiments, the temperature sensor provides the temperature information signals received at step 202 only in response to a triggering event. In some such embodiments, a triggering signal indicating occurrence of the triggering event is provided to the capsule, for example to the control element or to the temperature sensor, and step 202 is initiated in response to receipt of the triggering signal.

In some embodiments, the triggering signal may be provided by another sensor, such as a motion sensor providing a triggering signal indicating that a triggering motion was carried out by a user or by the subject on the capsule, or an illumination sensor providing a triggering signal indicating that the capsule has moved from a dark environment to an illuminated environment, or was taken out of its packaging.

Operation of the vibrating agitator in the vibrating mode of operation at step 207 effects vibration of the housing of the capsule, as described hereinabove, such that the housing exerts vibrations on the environment surrounding the capsule. Specifically, vibration of the capsule housing may be intended to effect a mechanical stimulation of the wall of the gastrointestinal tract.

A treatment session as defined in steps 201 to 210 may be repeatedly administered to the subject as specified in the treatment protocol for the subject, which may be determined or obtained at step 200. In some embodiments, the treatment protocol includes administering a plurality of treatment sessions to the subject. In some embodiments, the treatment protocol includes administering at least one treatment session to the subject per week, over a treatment period of at least two weeks, at least at least three weeks, at least four weeks, at least five weeks, at least six weeks, or at least eight weeks. In some embodiments, the treatment protocol includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A vibrating ingestible capsule comprising:
(a) a housing;
(b) a vibrating agitator disposed within said housing and adapted such that, in a first vibrating mode of operation, said housing exerts vibrations on an environment surrounding said vibrating ingestible capsule;
(c) a power supply disposed within said housing and adapted to power said vibrating agitator;
(d) a timer;
(e) a temperature sensor adapted to provide temperature information signals with respect to a temperature in an area surrounding the vibrating ingestible capsule, over a period of time; and
(f) a control element disposed within said housing and adapted to:
receive said temperature information signals from said temperature sensor;
identify a current temperature-over-time pattern based on said temperature information signals received from said temperature sensor;
compare said current temperature-over-time pattern to a predetermined temperature-over-time pattern;
when said current temperature-over-time pattern matches a first portion of said predetermined temperature-over-time pattern, initiate said timer to track a predetermined delay time;
after said current temperature-over-time pattern matches an entirety of said predetermined temperature-over-time pattern, and after said predetermined delay time has elapsed from activation of said timer, activate said vibrating agitator to operate in said first vibrating mode of operation; and
when said current temperature-over-time pattern becomes mismatched from said predetermined temperature-over-time pattern, reset said timer and said current temperature-over-time pattern,
wherein said predetermined temperature-over-time pattern includes a first duration and a subsequent second predetermined duration, wherein during an entirety of said first duration, a first predetermined temperature is distinct, by more than one degree, from a human body temperature, and during an entirety of said second predetermined duration, a second predetermined temperature is stable, within one degree, at said human body temperature, said second predetermined duration being at least 15 minutes, and
wherein said first portion of said predetermined temperature over time pattern includes at least a transition from said first predetermined temperature to said human body temperature.

2. The vibrating ingestible capsule of claim 1, wherein said predetermined delay time elapses at the same time as said current temperature-over-time pattern matching said entirety of said predetermined temperature-over-time pattern, such that said control element is adapted to activate said vibrating agitator to operate in said first vibrating mode of operation immediately upon determining that said entirety of said current temperature-over-time pattern matches said predetermined temperature-over-time pattern.

3. The vibrating ingestible capsule of claim 1, wherein said predetermined delay time elapses after said current temperature-over-time pattern matching said entirety of said predetermined temperature-over-time pattern, such that said control element is adapted to activate said vibrating agitator to operate in said first vibrating mode of operation a third predetermined duration after determining that said current temperature-over-time pattern matches said entirety of said predetermined temperature-over-time pattern.

4. The vibrating ingestible capsule of claim 1, wherein said timer is functionally associated with said control element or with said temperature sensor, said timer being adapted to identify times at which said temperature information signals are provided by said temperature sensor or are received by said control element.

5. The vibrating ingestible capsule of claim 1, wherein said temperature sensor is adapted to begin providing said temperature information signals only in response to a triggering event, and wherein said vibrating ingestible capsule further comprises at least one other sensor operative to provide a triggering signal indicative of occurrence of said triggering event.

6. The vibrating ingestible capsule of claim 1, wherein said power supply is adapted to power said temperature sensor, and wherein a power of said power supply is sufficient to power said temperature sensor to provide said temperature information signals at a predetermined frequency for a duration of at least one month, at least three months, at least six months, or at least a year, while maintaining sufficient charge for operation of said vibrating agitator in said first vibrating mode of operation for at least a predetermined cumulative vibrating duration.

7. The vibrating ingestible capsule of claim 1, further comprising a sensor power supply, different from said power supply, adapted to power said temperature sensor to provide said temperature information signals at a predetermined frequency for a duration of at least one month, at least three months, at least six months, or at least a year.

8. A method of treating an ailment of the gastrointestinal tract of a subject, the method comprising:
    (a) providing to the subject a vibrating ingestible capsule according to claim 1; and
    (b) ingesting said vibrating ingestible capsule, by the subject.

9. The method of claim 8, further comprising, prior to said ingesting of said vibrating ingestible capsule by said subject, carrying out a triggering action identifiable by at least one other sensor forming part of said vibrating ingestible capsule, such that said at least one other sensor provides a triggering signal indicating occurrence of a triggering event.

10. The vibrating ingestible capsule of claim 1, wherein in said first vibration mode of operation, said vibrating agitator is configured to exert forces on said housing to attain a vibrational frequency within a range of 100 Hz to 500 Hz.

11. The vibrating ingestible capsule of claim 1, wherein said second predetermined duration is at least four hours.

12. The vibrating ingestible capsule of claim 1, wherein, during said entirety of said first duration, said first predetermined temperature is distinct, by more than three degrees, from said human body temperature.

13. The vibrating ingestible capsule of claim 1, wherein said timer is a clock.

* * * * *